United States Patent
Daners et al.

(10) Patent No.: US 7,244,255 B2
(45) Date of Patent: Jul. 17, 2007

(54) HIGH-FREQUENCY SURGICAL GENERATOR

(75) Inventors: Felix Daners, Schaffhausen (CH); Pavel Novak, Stetten (CH)

(73) Assignee: Storz Endoskop Produktions GmbH (DE)

(*) Notice: Subject to any disclaimer, the term of this patent is extended or adjusted under 35 U.S.C. 154(b) by 347 days.

(21) Appl. No.: 10/971,478

(22) Filed: Oct. 22, 2004

(65) Prior Publication Data

US 2005/0143725 A1    Jun. 30, 2005

Related U.S. Application Data

(63) Continuation of application No. PCT/DE03/01367, filed on Apr. 28, 2003.

(30) Foreign Application Priority Data

Apr. 26, 2002   (DE) ................. 102 18 895

(51) Int. Cl.
*A61B 18/10* (2006.01)
(52) U.S. Cl. .................. 606/39; 606/32; 606/33; 606/34; 606/37; 606/38; 606/40
(58) Field of Classification Search ............ 606/32–41
See application file for complete search history.

(56) References Cited

U.S. PATENT DOCUMENTS

| 4,727,874 A | 3/1988 | Bowers et al. ......... 128/303.13 |
| 6,090,106 A | 7/2000 | Goble et al. .................. 606/41 |
| 6,093,186 A | 7/2000 | Goble .......................... 606/34 |

FOREIGN PATENT DOCUMENTS

EP    1 082 944 A1    3/2001

*Primary Examiner*—Roy D. Gibson
*Assistant Examiner*—Alex Toy
(74) *Attorney, Agent, or Firm*—St. Onge Steward Johnston & Reens LLC

(57) ABSTRACT

A high-frequency generator for high-frequency surgery is driven by a d.c. voltage supply. This d.c. voltage supply has a first working mode for transferring energy in a direction of the high-frequency generator, and also a second working mode for transferring energy in an opposite direction. With this arrangement, a particularly fast and efficient regulation of output voltage of the generator is possible. Therefore a reliable first cut may be performed on different kinds of tissue without any coagulation. Furthermore, owing to a high efficiency, a particularly small constructional size can be achieved.

7 Claims, 1 Drawing Sheet

HIGH-FREQUENCY SURGICAL GENERATOR

CROSS REFERENCE TO RELATED APPLICATIONS

This application is a continuation of pending International Application No. PCT/DE03/01367 filed on Apr. 28, 2003, which designates the United States and claims priority from pending German Application No. 102 18 895.5 filed on Apr. 26, 2002.

BACKGROUND OF THE INVENTION

The invention relates to a generator for power generation for high-frequency surgery. In high-frequency surgery, human or animal body tissue is cut or coagulated by means of an electric current. High-frequency surgery is usable with extreme advantage, particularly with endoscopic operating techniques.

FIELD OF THE INVENTION

It is the purpose of high-frequency surgical generators to provide electrical energy for high-frequency surgery in such manner that a desired operation result is obtained. In order to minimize muscle and nerve irritation, high-frequency surgical generators supply high-frequency energy in a frequency range above 300 kHz. This high-frequency energy is usually introduced into tissue by means of an electrode. Strong heating of the tissue surrounding the electrode occurs at the site of introduction. If high energy is supplied within a short period of time, this results in a vaporization of cell fluid and a bursting of cells, so that the group of cells around the electrode disintegrates. The electrode can move almost freely through the tissue. If less energy is supplied for a long period of time, this results in a coagulation of the tissue, i.e. to congealing of protein. In this case, the cells die off and become a viscous mass.

As far as the introduction of high-frequency energy is concerned, basically a distinction is made between two arrangements.

In a monopolar arrangement, a cutting or coagulating electrode having a small surface for introducing current is disposed at the site of operation, and a "neutral" electrode of large surface for conducting current away is disposed at a different site on the body of a patient. Here the electrode surface is dimensioned to be large enough for no appreciable heat to be developed at the electrode.

A bipolar arrangement comprises a divided electrode with which an introduction of current and a conducting away of current occur at the site of the operation.

Dosing of the energy is of great importance, because this directly affects the result of the operation. If the generator supplies too little energy, then no cutting is possible, and if too much energy is supplied, then the cut edges are strongly coagulated, which in turn leads to difficult healing or increased risk of infection.

Therefore, it is the aim to introduce into the body as little energy as possible for a pure cutting process, and the minimum amount of energy needed for coagulation for a combined cutting and coagulating process.

DESCRIPTION OF THE PRIOR ART

For minimization of this energy, the U.S. Pat. No. 4,114,623 discloses a method for regulating the generator current by observations of the electric arc appearing during cutting. Here a start of cutting, or a transition to a different kind of tissue having different electrical properties, presents a special problem. Because a transition to a different kind of tissue involves almost the same problem as is set by a start of cutting, reference will be made in the following to only the start of cutting.

If cutting is started with too high power, an undesired coagulation will already occur at the site of cutting. In order to minimize this coagulation, DE 38 15 835 A1 proposes that the generator output voltage be limited. This prevents cutting from being started with too high generator power. If, instead of this, cutting is started with too low power, this will lead to no cutting process being performed by penetration of the electrode into the tissue, but rather to an undesired coagulation of the tissue surface. This will also make a further first cut more difficult. In order to ensure a safe first cut without dependence on the tissue, DE 41 35 184 A1 proposes that an increased generator power be supplied at the start of making a first cut. This increased emission of power can then be lowered to the value normally needed for cutting when an electric arc is detected.

However, when this is put into practice, it is hardly possible to avoid coagulation from occurring at the site of the first cut, because a lowering of the power emitted by conventional generators cannot occur rapidly enough. This will be illustrated using as an example a conventional generator for surgery, consisting of a d.c. supply followed by a power oscillator. In this case, in order to lower the generator output voltage, the output voltage of the d.c. line power unit must be lowered first. For this, filter capacitors must be discharged. Furthermore, energy must be removed from reactive elements of a filter circuit in the power oscillator.

It is known to use controlled load resistors for discharging the filter capacitors in line power units. For example, a load resistor may be connected in series with a power transistor parallel to the output terminals of the line power unit. For a lowering of voltage, the power transistor is controlled and discharges the filter capacitors of the line power unit. In hitherto known generator circuits, the time constant of the line power unit is substantially greater than the time constant for discharging the reactive elements in the filter circuit of the power oscillator, so that until now little attention has been given to an optimization of this time constant.

The solutions hitherto known involve relatively large time constants, so that at the start of cutting, or with changes of tissue a coagulation can be hardly avoided. Furthermore, they have a high power loss owing to the thermal losses in the power transistor and the resistance for discharging the filter capacitors of the line power unit.

In order to avoid coagulation at the start of cutting, or upon a change of tissue, a rapid regulation of the output voltage is absolutely necessary. Furthermore, modern high-frequency generators for surgery are intended to become progressively smaller and less expensive. By achieving a highly efficient regulation of the output voltage, it would be possible to dispense with an addition of heat-dissipating devices.

BRIEF SUMMARY OF THE INVENTION

The invention is based on the object of providing a high-frequency generator for surgery which makes possible a rapid regulation of the output voltage with high efficiency.

In accordance with the invention, this object is achieved by a high-frequency generator comprising a power oscillator for delivering high-frequency energy, the power oscillator being driven by a d.c. voltage supply that converts a first input voltage to a voltage needed to be supplied to the power oscillator. The d.c. voltage supply has at least two working modes, a first working mode being provided for transferring energy from the first input voltage to the supply of the power oscillator, and a second working mode being provided for transferring energy from the supply of the power oscillator back to the first input voltage.

The device in accordance with the invention comprises a high-frequency generator for high-frequency surgery This furthermore comprises at least one power oscillator for delivering high-frequency energy, which is driven by a d.c. voltage supply. This voltage supply converts a first input voltage to a voltage needed to be supplied to the power oscillator. The suitable power oscillators usually are of a very high efficiency and also have a low internal resistance, so that their output voltage is proportional to the input voltage. For controlling the output voltage of the high-frequency generator, the d.c. voltage supply also can be controlled. Therefore it may supply different output voltages, as required, according to pre-settings made by a control unit.

Now, a d.c. voltage supply in accordance with the invention has at least two working modes. A first working mode serves in a conventional manner to transfer the needed energy from the first input voltage to the supply of the power oscillator. To now make possible rapid changes of the output voltage in order to adapt it to the very rapidly changing operating situations, a further working mode is provided. This transfers energy from the supply of the power oscillator back to the first input voltage. In this working mode, the energy stores on the output side of the d.c. voltage supply, and also in the power oscillator, may be rapidly discharged. Thereby the output voltage of the d.c. voltage supply and therewith also the output voltage of the power oscillator may be lowered within shortest time.

A further advantageous embodiment of the invention consists in the power oscillator also having at least two working modes. In this, one working mode serves in a conventional manner to transfer energy to the output, whilst another working mode is provided to feed back the energy stored in the reactive elements into the d.c. voltage supply. Thereby the output voltage of the power oscillator may rapidly be decreased to low values, even at high load impedances. If a second working mode of this kind is not provided, then a release of the energy from the reactive elements can be made exclusively to the load, i.e. to the patient. This then leads to undesirable coagulations or burns. For these reasons, hitherto attempts were made to keep the energy stored in the reactive elements as small as possible. Because of the possibility of feeding back the energy, a new degree of freedom is now created for dimensioning and optimizing the filters or reactive elements in the output circuit of the power oscillator. A second working mode of this kind may be put into practice, for example, by an additional provision of auxiliary switches (power transistors) for discharging the reactive elements. In a similar way, a discharging of this kind may be achieved by means of a suitable counter-phase control of the final power stage. A prerequisite for this kind of feed-back is that the energy fed back into the d.c. power supply can be taken up by energy reservoirs of large dimensions, such as, for example, capacitors, or fed back further to its input.

Another advantageous embodiment of the invention consists of the d.c. voltage supply being designed as a modified Buck converter, wherein the recovery diode is replaced by a switch. On the one hand, this configuration results in improved efficiency, because modern switches such as, for example MOSFETs, have smaller losses than diodes, and on the other hand, in the possibility of inverse operation for feeding back energy.

A further advantageous embodiment of the invention consists of an additional provision of a voltage transformer as a power-factor correction-circuit. This converts a sine-shaped line voltage with high power factor ($\cos \phi \approx 1$) to a rectified first input voltage.

In an advantageous embodiment of the invention, the timings of the additionally supplied voltage transformer as a power-factor correction-circuit, and the d.c. power supply are synchronized. Owing to this synchronization, a relatively high ripple of the rectified first input voltage can be tolerated. This leads to no instabilities of the d.c. voltage supply, because the input voltage averaged over a clock period is always constant. Furthermore, owing to the synchronization, the ripple current in the capacitors is considerably reduced. Therefore, the energy-storing elements, in particular the filter capacitors may be of smaller dimensions, and more favorably priced. In addition, owing to the smaller current load, the service life of the capacitors is increased.

A further embodiment of the invention comprises a d.c. voltage supply that has at least one of its output parameters regulated by a state regulator. Output parameters of this kind are, for example, output voltage, output current, and also output power. For regulation, a state regulator of this kind uses not only actual values of the output parameters to be regulated, but also at least one additional actual value of a voltage or a current of an internal circuit component. Thus, preferably in the case a Buck converter being used, the current is detected via the inductance. By means of additional actual values of this kind, better regulating characteristics, such as greater stability, better precision of regulation, and higher regulating speeds may be achieved.

In another embodiment of the invention, additionally a controllable current sink or load is disposed at the output of the d.c. voltage supply to monitor the functioning of the d.c. voltage supply. By means of a load of this kind the functioning of the d.c. voltage supply, and also of the voltage and current measuring means may be checked without activating the power oscillator and thus without supplying power to the output terminals or to the patient's current circuit. For performing the check, a control unit activates the current sink or load, or a given load resistance is set. When the d.c. voltage supply is activated, its functioning may be checked by evaluating a voltage measurement or a current measurement.

BRIEF DESCRIPTION OF THE DRAWINGS

In the following the invention will be described by way of example, without limitation of the general inventive concept, with the aid of examples of embodiment with reference to the drawings.

FIG. 1 illustrates an example of a device in according to the invention. A generator 1 for high-frequency surgery (high-frequency surgery generator) comprises a d.c. voltage supply 3 for converting a first input voltage 4 to a voltage 5 for driving a power oscillator. From this, the power oscillator 2 generates a high-frequency signal that issues from its output 6. Here, for example, the d.c. voltage supply is provided with a state regulator. Furthermore, a controllable current sink or load is disposed at the output of the d.c. voltage supply for checking the functioning. In order to obtain a sine-shaped current uptake from the sine-shaped line voltage 8, a voltage transformer is additionally disposed ahead of the d.c. voltage supply as a power-factor correction-circuit 7.

FIG. 2 shows an example of a particularly suitable Buck converter. In this case, a first input voltage 4 is chopped with a first power switch 11 and filtered by the series inductance 13 and also the parallel capacitor 14, and supplied as a voltage 5 for driving the power generator. The recovery diode usually provided with Buck converters is here substituted by a second power switch 12 at the same position. As an alternative to this, the second power switch 12 could also be connected in parallel with the normally present recovery diode.

Figure 1:
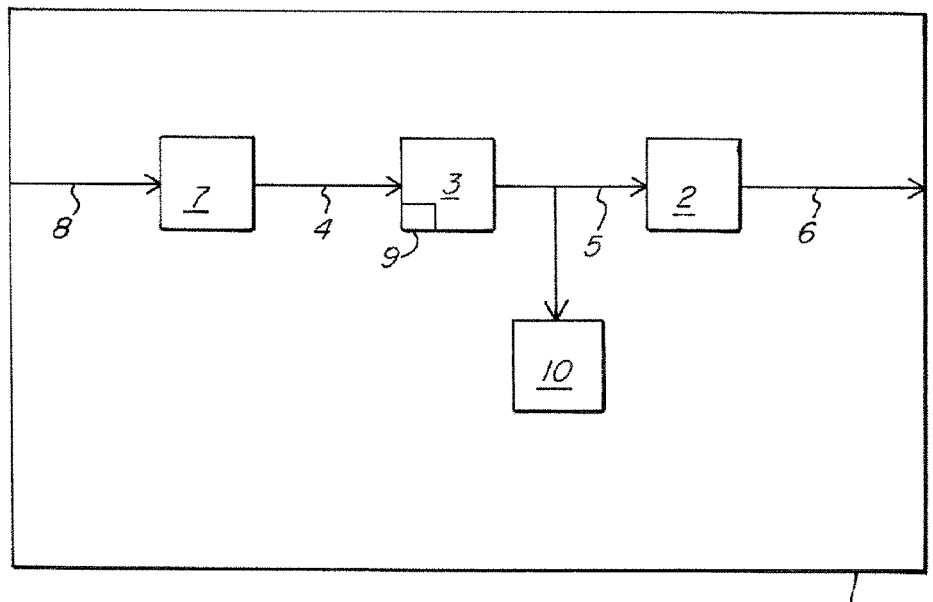
FIG. 1 schematically shows in a general form a device in accordance with the invention.
Figure 2:
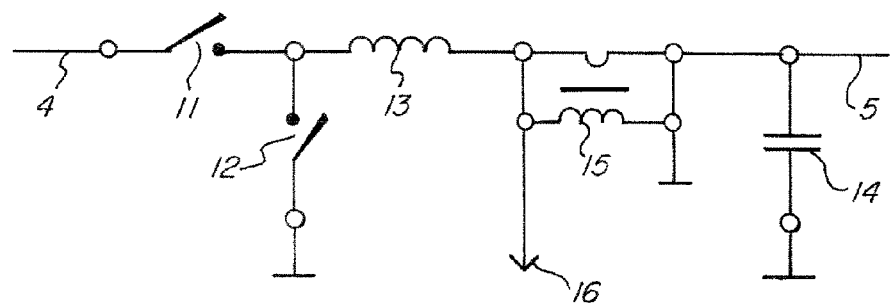
FIG. 2 shows an example of a specially advantageous d.c. voltage supply.

In the first working mode for energy transfer from the first input voltage 4 to the supply 5 of the power generator, the second power switch 12 may also remain open in case it has a diode connected in parallel in a manner that is usual with these converters. In a first switching phase the first power switch 11 is closed—the current continuing to flow through the series inductance 13 into the parallel capacitor 14. If now this first power switch is opened in a second switching phase, then the inductance will attempt to maintain the flow of current. The voltage at the switch-side end of the inductance commutates and thus becomes so negative that a diode disposed instead of, or parallel to, the second power switch 12 becomes conductive. If now a second power switch 12 parallel to the diode is turned on, then the losses of the arrangement can be substantially reduced, because modern power switches, such as for example MOSFETs, have substantially smaller losses than diodes. Because of their internal construction, MOSFETs as a rule have parasitic parallel diodes that can undertake the above-described functions.

In the second working mode for transfer of energy from the supply 5 of the power oscillator back to the first input voltage 4, the d.c. voltage supply can now be operated in the opposite direction like a boost transformer. With such transformers a diode is provided in place of the first power switch 11. The effect is analogous to that previously described and corresponds to the manner of working of known boost transformers.

Furthermore, a current transformer 15 is provided in series with the series inductance 13 for supplying a current-measuring signal 16 to the state regulator.

LIST OF REFERENCE SYMBOLS 1 high-frequency generator
2 power oscillator
3 d.c. voltage supply
4 first input voltage
5 voltage for supplying the power oscillator
6 output of the power oscillator
7 additional voltage transformer as a power-factor correction-circuit
8 sine-shaped line voltage
9 state regulator
10 current sink or load
11 first power switch
12 second power switch
13 series inductance
14 parallel capacitor
15 current transformer
16 current-measuring signal

What is claimed is:

1. High-frequency generator for high-frequency surgery, comprising:
    a power oscillator (2) for delivering high-frequency energy; and a d.c. voltage supply for driving the power oscillator, the d.c. voltage supply converting a first input voltage to a voltage needed to be supplied to the power oscillator;
    wherein the d.c. voltage supply has at least two working modes, a first working mode being provided for transferring energy from the first input voltage to the supply of the power oscillator, and a second working mode being provided for transferring energy from the supply of the power oscillator back to the first input voltage.

2. High-frequency generator according to claim 1, wherein the power oscillator has at least one first working mode for delivering high-frequency energy to an output, and a second working mode for feeding back energy stored in reactive elements into the d.c. power supply.

3. High-frequency generator according to claim 1, wherein the d.c. voltage supply is designed to be a modified buck converter in which a recovery diode is replaced by a switch.

4. High-frequency generator according to claim 1, wherein a voltage transformer is additionally supplied as a power-factor correction-circuit for converting a sine-shaped line voltage to a rectified first input voltage.

5. High-frequency generator according to claim 4, wherein timings of the voltage transformer additionally supplied as a power-factor correction circuit, and of the d.c. voltage supply are synchronized.

6. High-frequency generator according to claim 1, wherein a state regulator is provided for regulating the d.c. power supply, the state regulator performing a regulation by making use not only of an output voltage or an output current of the d.c. voltage supply as measured variables, but also of voltage or current values of internal components.

7. High-frequency generator according to claim 1, wherein a controllable current sink or load is additionally disposed at an output of the d.c. voltage supply for monitoring a functioning of the d.c. voltage supply.

* * * * *